US012295663B2

United States Patent
Pfister et al.

(10) Patent No.: US 12,295,663 B2
(45) Date of Patent: May 13, 2025

(54) METHOD FOR PROVIDING A COLLISION MODEL AND SYSTEM

(71) Applicant: Siemens Healthcare GmbH, Erlangen (DE)

(72) Inventors: Marcus Pfister, Bubenreuth (DE); Philipp Roser, Erlangen (DE)

(73) Assignee: Siemens Healthineers AG, Forchheim (DE)

(*) Notice: Subject to any disclaimer, the term of this patent is extended or adjusted under 35 U.S.C. 154(b) by 0 days.

(21) Appl. No.: 18/370,377

(22) Filed: Sep. 19, 2023

(65) Prior Publication Data
US 2024/0090948 A1 Mar. 21, 2024

(30) Foreign Application Priority Data
Sep. 20, 2022 (DE) .................. 10 2022 209 888.9

(51) Int. Cl.
*A61B 34/10* (2016.01)
*G06K 9/00* (2022.01)
(Continued)

(52) U.S. Cl.
CPC .............. *A61B 34/10* (2016.02); *G06V 40/10* (2022.01); *G16H 30/20* (2018.01);
(Continued)

(58) Field of Classification Search
CPC .. G06K 9/00; A61B 6/12; A61B 34/10; A61B 35/12
(Continued)

(56) References Cited

U.S. PATENT DOCUMENTS

2006/0274888 A1* 12/2006 Bernhardt .......... G05B 19/4061
378/117
2012/0238871 A1* 9/2012 Pfister ...................... A61B 6/12
600/431
(Continued)

FOREIGN PATENT DOCUMENTS

| CN | 114974548 A | 8/2022 |
|----|-------------|--------|
| DE | 102018209691 A1 | 12/2019 |
| WO | 2021198080 A1 | 10/2021 |

OTHER PUBLICATIONS

Breininger, K.; Pfister, M. et al: "Estimation of femoral artery access location for anatomic deformation correction" Pattern Recognition Lab, Department of Computer Science, Friedrich-Alexander-Universitat Erlangen-Nurnberg, http://www5.cs.fau.de; pp. 1.
(Continued)

*Primary Examiner* — Seyed H Azarian
(74) *Attorney, Agent, or Firm* — Lempia Summerfield Katz LLC

(57) ABSTRACT

A method for providing a collision model includes detecting an item of patient information that has an item of information on a spatial placement of an entry point of a medical object into an object undergoing examination. The item of patient information is registered with a movable medical device. The method also includes detecting an item of object information that has an item of information on a geometry and spatial position of a manipulator for moving the medical object. The manipulator includes a motion device and/or a member of technical medical personnel. A relative placement of the manipulator in relation to the object undergoing examination is determined based on the item of patient information and the item of object information. The collision model is provided for the purpose of moving the medical device based on the relative placement and the item of object information.

18 Claims, 5 Drawing Sheets

(51) Int. Cl.
  *G06V 40/10* (2022.01)
  *G16H 30/20* (2018.01)
(52) U.S. Cl.
  CPC ... *A61B 2034/102* (2016.02); *A61B 2034/105* (2016.02); *G06V 2201/03* (2022.01)
(58) Field of Classification Search
  USPC ........ 382/100, 103, 106–107, 128–132, 153, 382/155, 162, 168, 173, 181, 189, 199, 382/219, 224, 254, 276, 286–291, 305, 382/312; 600/424, 431; 378/4, 21, 117
  See application file for complete search history.

(56) References Cited

U.S. PATENT DOCUMENTS

| | | | |
|---|---|---|---|
| 2015/0190204 A1* | 7/2015 | Popovi .................... | A61B 5/061 600/424 |
| 2017/0220709 A1 | 8/2017 | Wan et al. | |
| 2019/0096520 A1 | 3/2019 | Strobel | |
| 2019/0261932 A1* | 8/2019 | Divoky .................. | B25J 9/1674 |
| 2020/0085281 A1* | 3/2020 | Regensburger .. | A61B 1/000095 |
| 2020/0219253 A1 | 7/2020 | Magaraggia et al. | |
| 2021/0093407 A1 | 4/2021 | Fredrickson | |
| 2021/0174502 A1* | 6/2021 | Siewerdsen .......... | A61B 6/4441 |
| 2021/0299471 A1 | 9/2021 | Yang | |
| 2022/0270247 A1 | 8/2022 | Wiets | |

OTHER PUBLICATIONS

Chun Albert K. et al; Principles of Arterial Access, Radiology Key, Chapter 27; 2015; pp. 1-5.

Siemens Healthcare GmbH; Corindus Vascular Robotics; https://www.corindus.com/corpath-grx/how-it-works; Jun. 2022; 12 pp.

Toggweiler, Stefan et al.; "Management of Vascular Access in Transcatheter Aortic Valve Replacement: Part 1: Basic Anatomy, Imaging, Sheaths, Wires, and Access Routes"; JACC: Cardiovascular Interventions, vol. 6, Issue 7, 2013, pp. 643-653, https://doi.org/10.1016/j.jcin.2013.04.003.

Workflow with CorPath GRX: YouTube video, Feb. 11, 2019, https://www.youtube.com/watch?v=p7UNJRoVNOw.

Zhong, Xia, et al. "A machine learning pipeline for internal anatomical landmark embedding based on a patient surface model." International journal of computer assisted radiology and surgery 14.1; 2019, pp. 53-61.

Breininger, K., et al. "Estimation of femoral artery access location for anatomic deformation correction." Proc Conf Image-Guid Interv Fokus Neuroradiol. 2017. pp. 1-1.

Decision to Grant Germany Application No. 10 2022 209 888.9 on Jul. 25, 2023, with English translation.

German Office Action for German Application No. 10 2022 209 888.9 mailed Jun. 27, 2023, with English translation.

* cited by examiner

METHOD FOR PROVIDING A COLLISION MODEL AND SYSTEM

This application claims the benefit of German Patent Application No. DE 10 2022 209 888.9, filed on Sep. 20, 2022, which is hereby incorporated by reference in its entirety.

BACKGROUND

The present embodiments relate to a method for providing a collision model, to a system, and to a computer program product.

In minimally invasive inventions, therapies such as the installation of stents, or diagnostics such as the detection of stenoses, are frequently carried out using medical objects that are introduced into the body. These medical objects are conventionally advanced to their location of use via guide wires and catheters, by access into the groin (e.g., the femoral artery) or the left armpit (e.g., radial access through the subclavian artery). Navigation to the individual branches of vessels is frequently performed by turning and advancing the guide wire or catheter at the point of entry.

If procedures of this kind are supported by a robotic motion device (e.g., a catheter robot and/or a vascular navigation robot), then the motion device frequently takes on manipulation of the medical object. A problem that arises when the motion device is arranged in the spatial vicinity of an object undergoing examination is that of preventing a collision between the motion device and a medical imaging device that is arranged on or around the object undergoing examination for the purpose of imaging the object undergoing examination and/or monitoring the procedure. If the motion device is operated remotely by a member of technical medical personnel, visual monitoring of the arrangement of the medical imaging device, the object undergoing examination, and/or the motion device, for the purpose of avoiding collision, may disadvantageously be made more difficult. Further, even in the event of manual and/or semi-automatic manipulation of the medical object (e.g., by the technical medical personnel), collisions between the technical personnel and the medical imaging device are to be avoided.

SUMMARY AND DESCRIPTION

The scope of the present invention is defined solely by the appended claims and is not affected to any degree by the statements within this summary.

The present embodiments may obviate one or more of the drawbacks or limitations in the related art. For example, avoidance of collision between a movable medical device and a manipulator for moving a medical object may be improved.

In a first aspect, the present embodiments relate to a method for providing a collision model. In a first act, an item of patient information is detected, which has an item of information on a spatial placement of an entry point of a medical object into an object undergoing examination. In this context, the item of patient information is registered with a movable medical device. In a further act, an item of object information is detected, which has an item of information on a geometry and spatial position of a manipulator for moving the medical object. In this context, the manipulator includes a, for example, robotic motion device and/or a member of technical medical personnel. In a further act, a relative placement of the manipulator in relation to the object undergoing examination is determined based on the item of patient information and the item of object information. Further, the collision model is provided for the purpose of moving the medical device at least based on the relative placement.

Detection of the item of patient information may include a capture and/or receiving of the item of patient information. Detection of the item of patient information may, for example, be performed using a detection unit such as a patient sensor and/or a medical imaging device. The patient sensor may include, for example, an optical and/or acoustic and/or electromagnetic sensor. Receiving of the item of patient information may include, for example, detection and/or read-off of a computer-readable data store and/or receiving from a data storage unit such as a database. As an alternative or in addition, the item of patient information may be detected with the aid of a user input by a member of the technical medical personnel.

The item of patient information may have an item of information (e.g., spatial coordinates) for the purpose of spatially placing the entry point of the medical object in the object undergoing examination. The entry point may include an entry site and an entry channel. Spatial placement of the entry point may include a spatial position of the entry point. As an alternative, spatial placement of the entry point may include a spatial position and alignment of the entry point (e.g., a spatial position of the entry site and spatial alignment of the entry channel). Further, the item of patient information may have image data (e.g., preoperative and/or intraoperative image data) and/or a patient model of the object undergoing examination. In this context, placement of the entry point may be determined (e.g., predetermined) with reference to the image data and/or the patient model. As an alternative or in addition, placement of the entry point may be determined at least based on the image data and/or the patient model.

The object undergoing examination may be, for example, a human and/or animal patient and/or a phantom for examination such as a vessel phantom. The medical object may be configured, for example, as a, for example, elongate surgical and/or diagnostic instrument. For example, the medical object may be configured such that the medical object is, at least in certain regions, flexible and/or rigid. The medical object may be configured, for example, as a needle (e.g., a puncture needle) and/or a catheter and/or endoscope and/or guide wire.

The movable medical device may include a medical imaging device and/or a medical treatment device. In this context, the medical device may be at least partly (e.g., fully) movable (e.g., by translation and/or rotation) in relation to the motion device. The item of patient information (e.g., the item of information on spatial placement of the entry point) is registered with the movable medical device (e.g., a coordinate system of the medical device). For example, a positional relationship may be defined between the entry point and the medical device, such as a relative placement.

Detection of the item of object information may include capture and/or receiving of the item of object information. Detection of the item of object information may be performed, for example, using the detection unit, such as an object sensor and/or the patient sensor. The object sensor may include, for example, an optical and/or acoustic and/or electromagnetic sensor. In this context, the detection unit may be configured to directly and/or indirectly detect the item of object information (e.g., the geometry) of the manipulator. The detection unit may, for example, detect imaging of the manipulator and determine the geometry from the imaging (e.g., by identifying a contour of the manipulator in the imaging). In this context, the detection unit (e.g., the object or patient sensor) may include a camera. As an alternative or in addition, the detection unit may detect an identifier of the manipulator, such as a barcode and/or QR code and/or RFID transponder. In this context, the item of object information may be provided by the identifier. As an alternative or in addition, the item of object information may be received with the aid of an item of identification information that is provided by the identifier (e.g., from a database and/or object catalog).

Receiving of the item of object information may, for example, include detection and/or read-off of a computer-readable data store and/or receiving from a data storage unit such as a database. As an alternative or in addition, the item of object information may be detected with the aid of a further user input by a member of the technical medical personnel. As an alternative or in addition, the item of object information may be provided by the manipulator.

In one embodiment, the item of object information has an item of information on the geometry and spatial position of the manipulator. In one embodiment, the geometry may describe a, for example, external shape and/or envelope and/or alignment and/or posture of the manipulator and/or a positional relationship of the proximal portion of the medical object in relation to the manipulator. In this context, the manipulator includes a, for example, robotic motion device and/or the technical medical personnel (e.g., a doctor) for moving (e.g., translation and/or rotation) of the medical object. The motion device may be, for example, a robotic device for remote manipulation of the medical object (e.g., a catheter robot). In one embodiment, the manipulator may act on a proximal portion of the medical object in order to place and/or to replace a distal portion of the medical object. In this context, at least part of the medical object (e.g., the distal portion of the medical object) may be introduced into the object undergoing examination (e.g., into a hollow organ and/or tissue of the object undergoing examination) at the entry point (e.g., via an introducer sheath). In one embodiment, the item of object information may be spatially resolved in two dimensions (2D) or three dimensions (3D). The item of object information may have, for example, a representation (e.g., a model) and/or an imaging of the manipulator. Further, the item of object information may be detected repeatedly. The representation of the manipulator may include, for example, a skeletonized model and/or a volume mesh model and/or a computer-aided design (CAD) model.

In one embodiment, the relative placement (e.g., a relative position and/or alignment and/or posture) of the manipulator in relation to the object undergoing examination (e.g., the entry point) may be determined based on the item of patient information (e.g., the spatial position of the entry point) and the item of object information (e.g., the spatial position of the manipulator). Because the item of patient information is registered with the medical device (e.g., the coordinate system of the medical device) and using the relative placement of the manipulator in relation to the object undergoing examination (e.g., the entry point), it is further possible to determine a further relative placement of the manipulator in relation to the medical device.

In one embodiment, the collision model may be provided based on the relative placement (e.g., the further relative placement) and the item of object information. The collision model may have an item of information on a distance (e.g., a distance at that instant) and, for example, a distance field between the medical device and the manipulator (e.g., between the manipulator and the medical object). Further, the collision model may have an item of information on a spatial region (e.g., a volume in which the manipulator, such as the manipulator and the medical object, are arranged).

In one embodiment, using the provided collision model, a movement of the medical device may be adapted (e.g., diverted or stopped) in order to avoid making contact (e.g., touching and/or collision) between the medical device and the manipulator.

In a further embodiment of the method, detection of the item of patient information may include capture and/or receiving of preoperative image data and/or of a patient model of the object undergoing examination. Further, an item of planning information on a planned procedure and/or a planned placement of the entry point may be detected. In this context, placement of the entry point may be determined using the item of planning information and the preoperative image data and/or the patient model.

In one embodiment, the preoperative image data may be captured using the medical device (e.g., the medical imaging device) or a further medical imaging device. As an alternative or in addition, the preoperative image data may be provided by a providing unit of the medical imaging device for the purpose of capturing the preoperative image data. As an alternative or in addition, receiving of the preoperative image data may include detection and/or read-off of a computer-readable data store and/or receiving from a data storage unit such as a database.

The preoperative image data may have imaging of the object undergoing examination with spatial resolution in 2D or 3D. Further, the preoperative image data may have temporal resolution. In this context, the preoperative image data may image the object undergoing examination preoperatively (e.g., prior to the medical object being arranged in the object undergoing examination). For example, the preoperative image data may include a preoperative 3D data set in CT angiography.

As an alternative, detection of the item of patient information may include receiving of a patient model. The patient model may include, for example, an individual (e.g., adapted) generic or statistical model of the object undergoing examination. In this context, the patient model may have a representation with spatial resolution in 2D or 3D (e.g., a skeletonized model and/or a volume model, such as a volume mesh model) of the object undergoing examination.

Detection of the item of planning information may, for example, include detection and/or read-off of a computer-readable data store and/or receiving from a data storage unit such as a database. As an alternative or in addition, the item of planning information may be detected using a further user input by a member of the technical medical personnel. As an alternative or in addition, the item of planning information may be provided by the manipulator.

The item of planning information may include an item of information on a planned procedure (e.g., on a sequence and/or a site of treatment and/or an objective of treatment). As an alternative or in addition, the item of planning information may have an item of information on the planned spatial placement (e.g., a planned spatial position and/or alignment) of the entry point (e.g., in relation to the item of patient information and/or the object undergoing examination).

The placement (e.g., the actual placement) of the entry point may be determined based on the item of planning information (e.g., the item of information on the planned procedure and/or the planned placement of the entry point), and the preoperative image data and/or the patient model.

Determining the position of the entry point may include registering the item of planning information with the item of patient information.

According to a first variant, placement of the entry point may be determined (e.g., automatically) using the item of information on the planned procedure. For example, a standard placement of the entry point for the planned procedure may be received from a data storage unit and/or a database. In this context, the standard placement may be adapted to the object undergoing examination using the item of patient information (e.g., the preoperative image data and/or the patient model). According to a second variant, placement of the entry point may be determined by identification of the planned placement of the entry point in the preoperative image data and/or the patient model, and the registration between the item of patient information and the item of planning information.

Using the embodiment, it is possible to enable determination of placement of the entry point in a manner based on planning (e.g., on workflow).

In a further embodiment of the method, detection of the item of patient information may include capture and/or receiving of intraoperative image data of the object undergoing examination. In this context, imaging of at least a portion of the medical object and/or imaging of an introducer sheath for introducing the medical object into the object undergoing examination may be identified in the intraoperative image data. Further, the placement of the entry point may be determined using the identified imaging.

In one embodiment, the intraoperative image data may be captured using the medical device (e.g., the medical imaging device) or a further medical imaging device. As an alternative or in addition, the intraoperative image data may be provided by a providing unit of the medical imaging device for the purpose of capturing the intraoperative image data. As an alternative or in addition, receiving of the intraoperative image data may include detection and/or read-off of a computer-readable data store and/or receiving from a data storage unit such as a database.

The intraoperative image data may have imaging of the object undergoing examination with spatial resolution in 2D and/or 3D. Further, the intraoperative image data may have temporal resolution. In this context, the intraoperative image data may image the object undergoing examination intraoperatively (e.g., while the medical object is arranged over the entry point in the object undergoing examination).

Identification of imaging of the at least one portion (e.g., the distal portion) of the medical object, and/or imaging of the introducer sheath may include identification (e.g., segmentation) of image points (e.g., pixels and/or voxels) of the intraoperative image data that images the at least one portion of the medical object and/or the introducer sheath. For example, to do this, image values of the image points of the intraoperative image data may be compared with a predetermined threshold value. As an alternative or in addition, an algorithm may be applied to the intraoperative image data for the purpose of object and/or pattern recognition. This algorithm is configured to identify imaging of the at least one portion of the medical object and/or imaging of the introducer sheath using geometric features of the medical object and/or the introducer sheath that are imaged in the intraoperative image data. The geometric features may include, for example, a contour and/or shape and/or edge and/or corner and/or contrast.

In one embodiment, placement of the entry point may be determined using the identified imaging. In the case of identifying imaging of the introducer sheath, placement of the entry point in a pre-defined positional relationship to imaging of the introducer sheath (e.g., to geometric features of the introducer sheath) may be determined, for example, as a geometric center point of an opening in the introducer sheath. As an alternative or in addition, placement of the entry point may be determined using the identified imaging of the at least one portion (e.g., the distal portion) of the medical object. In this context, determining the placement of the entry point may further include the identification of imaging of anatomical features of the object undergoing examination (e.g., a tissue boundary and/or a hollow organ) that are imaged in the intraoperative image data. In this context, placement of the entry point may be determined in a pre-defined positional relationship to imaging of the anatomical features and/or the at least one portion of the medical object.

The embodiment may enable particularly reliable (e.g., secure) determining of placement of the entry point.

In a further embodiment of the method, a 2D imaging of the introducer sheath may be identified in the intraoperative image data. In this context, a spatial position and an azimuthal angle of the introducer sheath may be determined using the 2D imaging of the introducer sheath. In one embodiment, the item of object information may have an item of information on a geometry of the introducer sheath. In this context, an altitude angle of the introducer sheath may be determined using the 2D imaging of the introducer sheath and the item of object information. In this context, the relative placement may be determined based on the position of the introducer sheath, the azimuthal angle, the altitude angle, and the item of object information.

In one embodiment, the intraoperative image data may define an imaging plane, such as a plane of the 2D imaging of the introducer sheath. In this context, first, the position of a pre-defined portion of the introducer sheath, such as a sheath tip, in the intraoperative image data may be identified. Using the identified 2D imaging of the introducer sheath (e.g., using identified geometric features of the introducer sheath) in the intraoperative image data, it is possible to determine the azimuthal angle of the introducer sheath in the imaging plane and at the position of the pre-defined portion of the introducer sheath (e.g., at the entry point).

The item of object information may additionally have the item of information on the geometry of the introducer sheath. In this context, the geometry of the introducer sheath may describe, for example, an external shape and/or structure and/or an arrangement (e.g., a position and/or alignment and/or posture) and/or structural features (e.g., a contour and/or edge and/or corner and/or opening) of the introducer sheath.

In one embodiment, the intraoperative image data may have a 2D imaging of the structural features of the introducer sheath. With the aid of the intraoperative 2D imaging of the introducer sheath (e.g., the structural features) and the item of object information (e.g., the item of information on the geometry of the introducer sheath), it is possible to determine the altitude angle of the introducer sheath in relation to the imaging plane and at the position of the pre-defined portion of the introducer sheath (e.g., at the entry point).

In this context, the entry point (e.g., the entry site) may form a reference point (e.g., a vertex) of the azimuthal and altitude angles. Further, a longitudinal axis in a coronal plane of the object undergoing examination may form a reference side of the azimuthal angle. Further, a longitudinal axis in a sagittal plane of the object undergoing examination may form a reference side of the altitude angle.

The embodiment may enable determination of the relative placement in 3D using the 2D imaging of the introducer sheath. In this context, an item of depth information (e.g., the altitude angle) may be determined by additionally taking into account the item of object information (e.g., the item of information on the geometry of the introducer sheath).

In a further embodiment of the method, identification of the imaging of the at least one portion of the medical object and/or the introducer sheath in the intraoperative image data may include identification of a marker structure. Further, the item of object information may also have an item of information on a geometry and/or arrangement of the marker structure on the medical object and/or the introducer sheath.

Identification of the imaging of the at least one portion (e.g., the distal portion) of the medical object and/or the imaging of the introducer sheath may include identification (e.g., segmentation) of image points (e.g., pixels and/or voxels) of the intraoperative image data that images the marker structure. For example, to do this, image values of the image points of the intraoperative image data may be compared with a predetermined threshold value. As an alternative or in addition, an algorithm may be applied to the intraoperative image data for the purpose of object and/or pattern recognition. This algorithm is configured to identify imaging of the marker structure using geometric features of the marker structure that are imaged in the intraoperative image data. The geometric features may include, for example, a contour and/or shape and/or edge and/or corner and/or contrast of the marker structure.

In one embodiment, the item of object information may also have the item of information on the geometry (e.g., a shape and/or size) and/or arrangement (e.g., position and/or relative position and/or positional relationship and/or alignment and/or posture) of the marker structure on the medical object and/or the introducer sheath. Using the item of information on the geometry of the marker structure may make it possible to improve identification of the imaging of the marker structure. Based on the item of information on the arrangement of the marker structure on the medical object and/or the introducer sheath, the position of the entry point may be determined using the identified imaging of the marker structure.

The embodiment may enable improved (e.g., more robust and/or more reliable) identification of the imaging of the at least one portion of the medical object and/or the introducer sheath in the intraoperative image data.

In a further embodiment of the method, the intraoperative image data may have at least two images of the at least one portion of the medical object and/or at least two images of the introducer sheath, respectively from different imaging directions. In this context, a spatial position and alignment of the at least one portion of the medical object and/or the introducer sheath may be determined using the respective at least two images. Further, the relative placement may be determined based on the position and alignment of the at least one portion of the medical object and/or the introducer sheath and the item of object information.

In one embodiment, the intraoperative image data may image the at least one (e.g., distal) portion of the medical object and/or the introducer sheath from at least two different (e.g., not collinear) imaging directions (e.g., directions of projection). Using the at least two images, it is possible, for example, by filtered back projection to determine a 3D placement (e.g., the position and alignment) of the at least one portion of the medical object and/or the introducer sheath. In this context, the placement of the at least one portion of the medical object and/or the introducer sheath in relation to the object undergoing examination may be determined (e.g., in a coordinate system of the object undergoing examination).

In one embodiment, the relative placement may be determined based on the placement (e.g., the position and alignment) of the at least one portion of the medical object and/or the introducer sheath and the item of object information (e.g., the geometry of the manipulator). For example, the relative placement may be determined using the item of information on the arrangement and/or positional relationship of the proximal portion of the medical object in relation to the manipulator and the placement of the distal portion of the medical object and/or the introducer sheath.

The embodiment may enable 3D detection of the at least one portion of the medical object and/or the introducer sheath in the intraoperative image data. As a result, improved (e.g., more precise) determination of the relative placement may be enabled.

In a further embodiment of the method, the item of object information may include an item of information on a geometry of an external shape of the manipulator and/or a placement of the medical object on the manipulator.

In one embodiment, the item of object information may describe a geometry of the external shape of the manipulator (e.g., relating to the arrangement and/or size and/or configuration of structural features of the manipulator). The structural features may, for example, include a housing and/or contour and/or edge and/or corners and/or opening and/or protuberance and/or recess of the motion device. Further, the structural features may include a size and/or extent and/or contour of the technical personnel. As an alternative or in addition, the item of object information may have an item of information on the placement (e.g., the placement at that instant, such as the position and/or alignment and/or posture) of the medical object (e.g., the proximal portion of the medical object) on the manipulator (e.g., in relation to the manipulator). For example, the item of information may describe a positional relationship between the medical object and the manipulator. For example, the item of object information may describe an item of information on the placement of an exit site of the medical object on the motion device. For example, the motion device may move the medical object in translation and/or rotation, by exerting a force on the proximal portion of the medical object. To do this, the proximal portion of the medical object may be arranged at least partly in the motion device. For the purpose of receiving the proximal portion, the motion device may have, for example, a recess (e.g., in the form of a furrow and/or tunnel). In this context, the exit site may describe an opening in the motion device (e.g., the recess) that faces the object undergoing examination, and the medical object may exit from the receiving region of the motion device at this exit site.

The embodiment may enable improved (e.g., more precise) providing of the collision model.

In a further embodiment of the method, the object undergoing examination may be arranged on a patient support device. In this context, the manipulator may have a defined positional relationship relative to the patient support device. Further, the relative placement may also be determined based on the defined positional relationship.

The patient support device may include, for example, a patient rest and/or a patient table and/or a patient chair for supporting the object undergoing examination. In this context, the patient support device may be fixed in position or be movable (e.g., replaceable). In one embodiment, the manipulator may have a defined (e.g., known) positional relationship (e.g., position and alignment) relative to the patient support device.

The motion device may be secured to the patient support device by a securing unit such as a stand and/or robot arm. In this context, the securing unit may be configured to place and/or move and/or hold the motion device in a defined manner in relation to the patient support device. As an alternative or in addition, the securing unit may be configured to detect the placement (e.g., the placement at that instant, such as the positional relationship) of the motion device relative to the patient support device (e.g., by a sensor).

As an alternative or in addition, the placement (e.g., the placement at that instant, such as the position and/or alignment and/or posture) of the manipulator (e.g., of the motion device and/or the technical personnel) may be detected, for example, by the object sensor. By additionally detecting the placement of the patient support device and/or an arrangement of the object sensor in a defined positional relationship to the patient support device, the positional relationship of the manipulator relative to the patient support device may be determined.

As a result of additionally taking into account the defined positional relationship, it is possible to enable more precise determination of the relative placement. For example, placement of the object undergoing examination on the patient support device may be estimated and/or received. As a result, the positional relationship of the manipulator relative to the object undergoing examination (e.g., the entry point) may be determined.

In a further embodiment of the method, the movable medical device may include a medical imaging device and/or a medical treatment device.

In one embodiment, the medical imaging device may include a medical X-ray device (e.g., a medical C-frame X-ray device and/or an angiography device) and/or a computed tomography system (CT system) and/or a magnetic resonance imaging system (MRI system) and/or a positron emission tomography system (PET system) and/or an ultrasound device. In this context, the medical imaging device may be configured to capture the preoperative and/or intraoperative image data.

The medical treatment device may include, for example, an irradiation system and/or an ultrasound device such as a histotripsy device, and/or a surgical robot and/or a biopsy device.

The medical device (e.g., the medical imaging device and/or the medical treatment device) may be movable manually and/or automatically (e.g., by robot).

The embodiment may make it possible to avoid collision between the manipulator and the medical imaging device and/or the medical treatment device (e.g., during intraprocedural imaging and/or treatment of the object undergoing examination).

In a further embodiment of the method, a movement of the medical device may be controlled using the collision model such that no contact (e.g., no contact brought about by movement) is made between the medical device, the manipulator, and the medical object.

Control of the movement of the medical device may be manual, semi-automatic, or fully automatic. For example, the medical device may be moved manually by a member of the technical medical personnel or a further member of the technical medical personnel. In this context, control of the movement based on the collision model may include output of, for example, an acoustic and/or haptic and/or visual warning signal. In the case of movement of the medical device that is controlled semi-automatically or fully automatically, for example, a control signal may be provided to the medical device, depending on the collision model. Output of the warning signal may be selective (e.g., if the spacing between the medical device and the manipulator reaches or falls below a predetermined minimum). The control signal may be provided unselectively and/or selectively. In the case of unselectively providing the control signal, the movement of the medical device (e.g., a movement trajectory) may be prospectively adapted based on the collision model. In the case of selectively providing the control signal, the movement of the medical device may be slowed, stopped, or diverted (e.g., if the spacing between the medical device and the manipulator reaches or falls below the predetermined minimum).

The embodiment may enable secure (e.g., collision-free) movement of the medical device in the presence of the manipulator.

In a further embodiment of the method, providing the collision model may include identification of a forbidden spatial zone in which the manipulator is at least partly arranged. In this context, a movement of the medical device may be controlled using the collision model such that the medical device does not penetrate into the forbidden zone and/or become arranged in the forbidden zone.

The collision model may have an item of information on a relative placement (e.g., a relative position and/or a positional relationship) between the medical device and the manipulator. Further, the collision model may have the item of information on the distance (e.g., the distance at that instant) between the medical device and the manipulator. In one embodiment, the forbidden spatial zone, including a volume, may be identified. In this context, the manipulator may be arranged at least partly (e.g., fully) within the volume.

In addition, identification of the forbidden zone may be extended such that the medical object and/or the object undergoing examination and/or the patient support device are arranged at least partly (e.g., fully) in the forbidden zone.

In one embodiment, the movement of the medical device may be controlled using the collision model, for example, by outputting the warning signal and/or providing the control signal, such that the medical device does not penetrate into the forbidden zone and/or become arranged in the forbidden zone.

The embodiment may enable improved control of the movement of the medical device for the purpose of avoiding collision.

In a further embodiment of the method, the collision model may also be provided based on the item of object information. In this context, the forbidden zone may be identified using the geometry of the manipulator (e.g., as conical and/or cuboid and/or ellipsoidal and/or as a half-space).

In one embodiment, the forbidden spatial zone, including a volume, may be identified. The volume may be delimited, for example, by one or more boundary faces. For example, a volume of which the boundary face is at a predetermined minimum spacing from the manipulator (e.g., a surface of the manipulator) may be identified using the geometry of the manipulator as the forbidden zone. As an alternative or in addition, a boundary face may be established, using the geometry of the manipulator, which delimits the forbidden zone, at a predetermined point on the manipulator (e.g., the exit site), and at a predefined angle to the manipulator (e.g., as a tangential plane on a surface of the manipulator). In this context, a shape of the volume may be adapted to an external shape and/or a movement range and/or an arrangement range of the manipulator based on, for example, the item of object information (e.g., the geometry of the manipulator). For example, the volume may be identified as substantially conical, with a tip of the cone arranged at the exit site of the manipulator or at the entry point. As an alternative or in addition, the volume may be identified as a half-space (e.g., delimited by a planar boundary face). As an alternative or in addition, the volume may be identified as substantially cuboid (e.g., delimited by a plurality of planar boundary faces). As an alternative or in addition, the volume may be identified as substantially ellipsoidal (e.g., enveloping the manipulator).

The embodiment may enable a, for example, space-saving adaptation of the forbidden zone to the geometry of the manipulator. As a result, unnecessary constraints on the scope of movement of the medical device may be avoided.

In a second aspect, the present embodiments relate to a system, including a detection unit and a providing unit, where the system is configured to perform a method for providing a collision model. In this context, the detection unit is configured to detect the item of patient information and the item of object information. Further, the providing unit is configured to determine the relative placement and to provide the collision model.

The detection unit may include an object sensor and/or a patient sensor and/or a medical imaging device that are configured to detect (e.g., capture) the item of object information and/or the item of patient information. As an alternative or in addition, the detection unit may include an interface that is configured to receive the item of object information and/or the item of patient information.

The advantages of the system of the present embodiments correspond substantially to the advantages of the method of the present embodiments for providing a collision model. Features, advantages, or alternative embodiments that are mentioned in this context may likewise also be applied to the other subject matter, and vice versa.

In a further embodiment of the system, the system may also include the medical device. In this context, the medical device may be configured to be moved depending on the collision model such that no contact (e.g., no contact brought about by movement) is made between the medical device, the manipulator, and the medical object.

The medical device may be configured to be moved manually, semi-automatically, or fully automatically (e.g., to be controlled for the purpose of movement). For example, the medical device may be configured to be moved manually by a member of the technical medical personnel. In this context, control of the movement based on the collision model may include output of an in particular acoustic and/or haptic and/or visual warning signal. As an alternative or in addition, the medical device may be configured to be moved semi-automatically or fully automatically, depending on a control signal that is provided by the providing unit. The providing unit may be configured to provide the control signal to the medical device depending on the collision model. For example, the medical device may be configured to be moved depending on the collision model such that the possibility of contact (e.g., contact brought about by movement) between the medical device, the manipulator, and the medical object is ruled out.

In a further embodiment of the system, the movable medical device may include a medical imaging device and/or a medical treatment device.

The medical imaging device may include a medical X-ray device (e.g., a medical C-frame X-ray device) and/or a computed tomography system (CT system) and/or a magnetic resonance imaging system (MRI system) and/or a positron emission tomography system (PET system) and/or an ultrasound device. In this context, the medical imaging device may be configured to capture the preoperative and/or intraoperative image data.

The medical treatment device may include, for example, an irradiation system and/or an ultrasound device such as a histotripsy device, and/or a surgical robot and/or a biopsy device.

In a third aspect, the present embodiments relate to a computer program product, having a computer program that may be loaded directly into a memory of a providing unit, having program sections in order to perform all the acts of a method of the present embodiments for providing a collision model when the program sections are executed by the providing unit. In this context, the computer program product may include software having a source code that still needs to be compiled and bound or that need only be interpreted, or executable software code that still has to be loaded into the providing unit in order to be executed. As a result of the computer program product, the method for providing a collision model may be rapidly, identically reproducibly and robustly performed by a providing unit. The computer program product is configured such that the computer program product may perform the method acts according to the present embodiments using the providing unit.

The advantages of the computer program product correspond substantially to the advantages of the method of the present embodiments for providing a collision model. Features, advantages, or alternative embodiments that are mentioned in this context may likewise also be applied to the other subject matter, and vice versa.

Further, the present embodiments may take as its starting point a computer-readable storage medium and/or electronically readable data carrier on which program sections that are readable and executable by a providing unit are stored in order to perform all the acts of the method for providing a collision model when the program sections are executed by the providing unit. Implementation that is largely in software form has the advantage that providing units that have already been used hitherto may also be retrofitted in a simple manner by a software update in order to operate according to the present embodiments. A computer program product of this kind may include, in addition to the computer program, where appropriate, additional constituents such as documentation and/or additional components such as hardware components such as hardware keys (e.g., dongles, etc.) for the purpose of utilizing the software.

BRIEF DESCRIPTION OF THE DRAWINGS

Embodiments of the invention are illustrated in the drawings and described in more detail below. In different figures, like reference numerals are used for like features. In the drawings.

DETAILED DESCRIPTION

Figure 1:
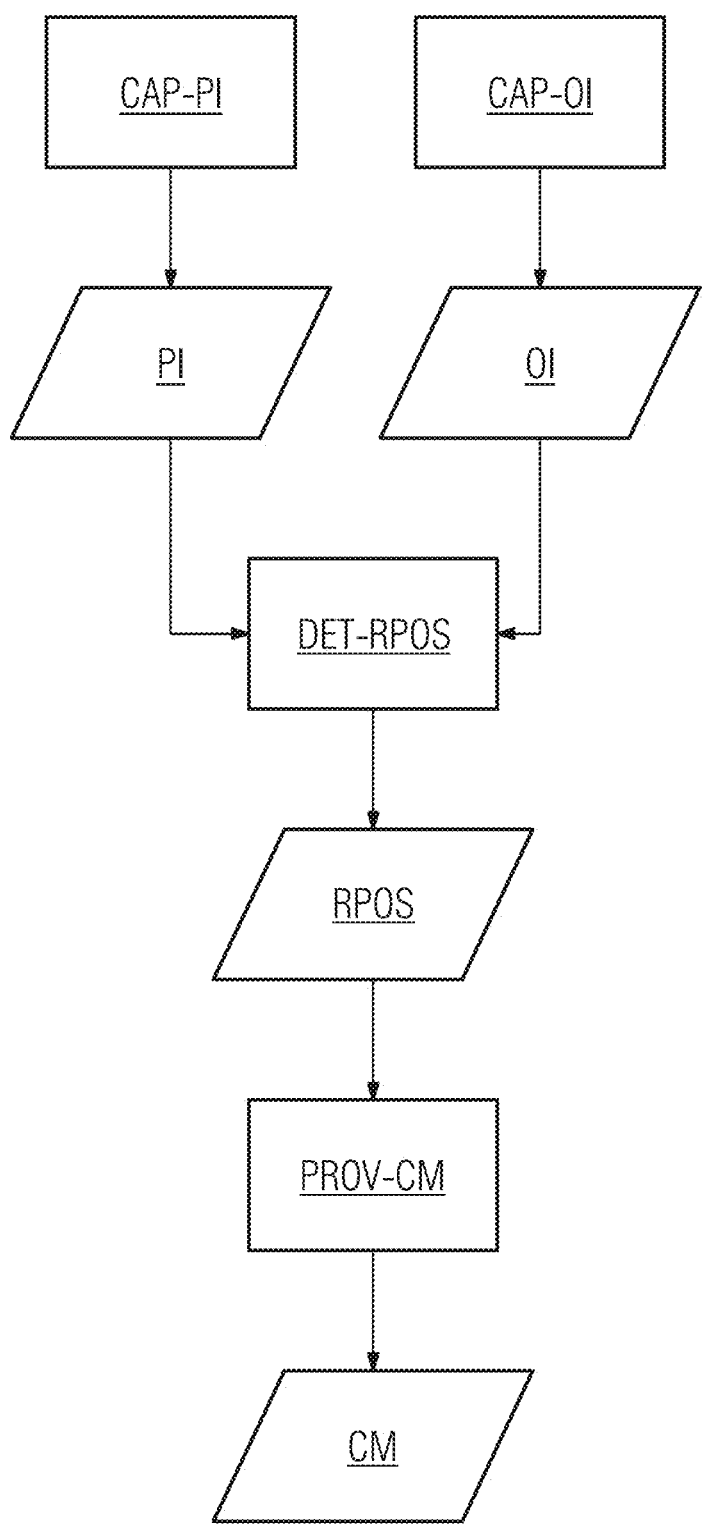
FIGS. 1 to 3 show schematic illustrations of different embodiments of a method for providing a collision model.

FIG. 1 schematically illustrates an embodiment of a method for providing a collision model PROV-CM. In this context, an item of patient information PI may be detected CAP-PI, and this has an item of information on a spatial placement of a, for example, axillary or radial entry point of a medical object into an object undergoing examination. In this context, the item of patient information PI may be registered with a movable medical device. The medical device may include a medical imaging device and/or a medical treatment device. Further, an item of object information OI may be detected CAP-OI, and this has an item of information on a geometry and spatial position of a manipulator for moving the medical object. In this context, the manipulator may include a motion device and/or a member of the technical medical personnel. Further, a relative placement RPOS of the manipulator in relation to the object undergoing examination may be determined DET-RPOS based on the item of patient information PI and the item of object information OI. In accordance with this, the collision model CM may be provided PROV-CM for the purpose of moving the medical device based on the relative placement RPOS and the item of object information OI. In one embodiment, a movement of the medical device may be controlled using the collision model CM such that no contact is made between the medical device, the manipulator, and the medical object.

In one embodiment, the item of object information OI may include an item of information on a geometry of an external shape of the manipulator and/or a placement of the medical object on the manipulator.

Figure 2:
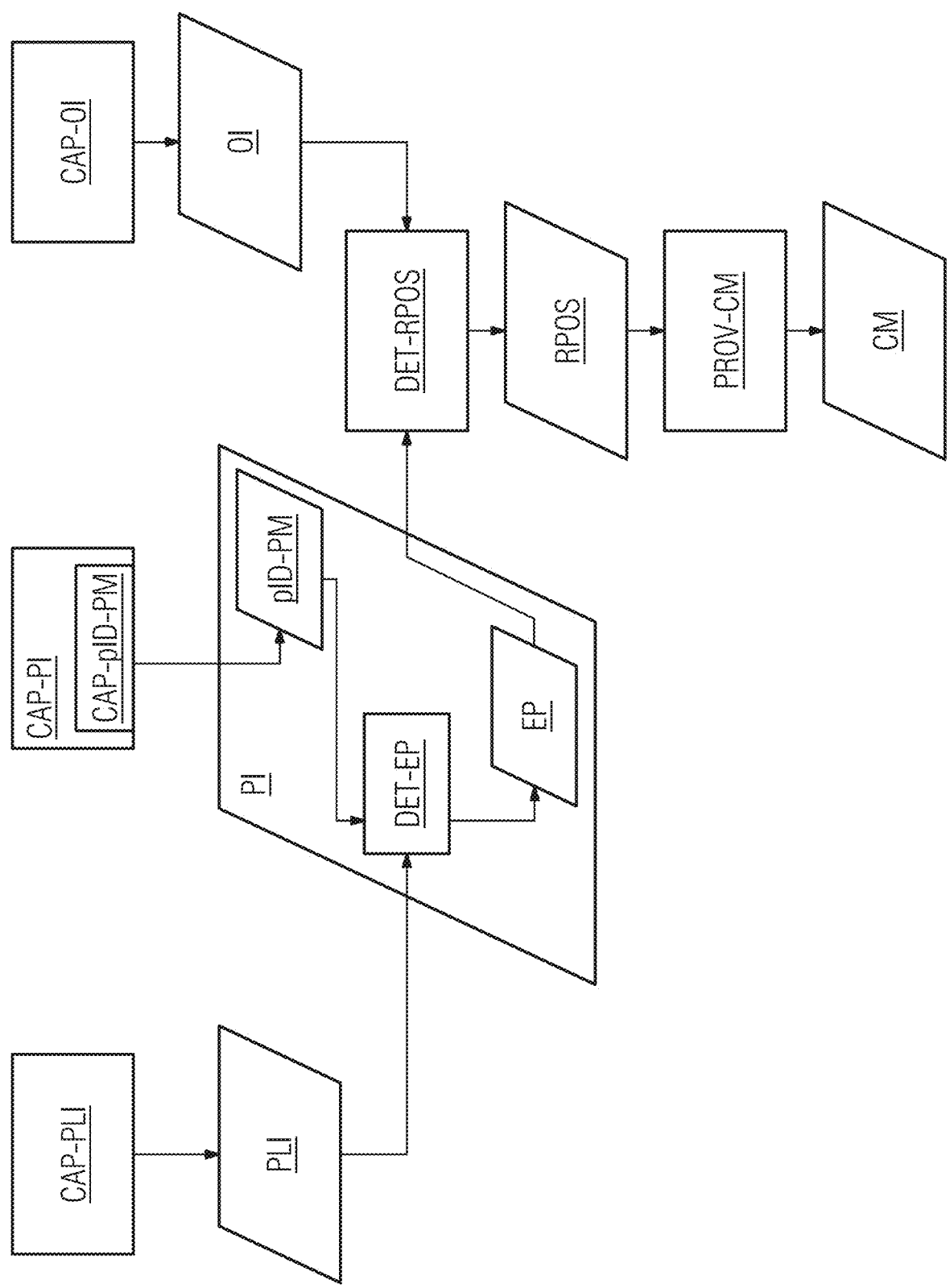

FIG. 2 shows a schematic illustration of a further embodiment of a method for providing a collision model PROV-CM. In this context, detection of the item of patient information CAP-PI may include capture and/or receiving CAP-pID-PM of preoperative image data and/or a patient model pID-PM of the object undergoing examination. Further, an item of planning information PLI on a planned procedure and/or a planned position of the entry point may be detected CAP-PLI. In this context, the position of the entry point EP may be determined DET-EP using the item of planning information PLI and the preoperative image data and/or the patient model pID-PM.

Described below is an example of a sequence of the above-described embodiment of the method for a C-frame X-ray device as the medical device and a motion device as the manipulator. In a first act, the item of planning information PLI may specify a vascular intervention through the groin as a planned procedure. In this context, the common femoral artery in the groin of the object undergoing examination, about 2-5 cm below the skin, may be identified as the planned position of the entry point, as the point of the artery closest to the surface. The publication by Breininger et al., "Estimation of femoral artery access location for anatomic deformation correction," 3rd. Conference on Image-Guided Interventions, 2017, describes, for example, a method for estimating the position of the entry point using a course taken by a vessel, derived from the preoperative image data, such as a three-dimensional (3D) data set of a CT angiography, with deviation usually below 10 mm. Further, a direction of puncture may also be determined using the course of the vessel (e.g., as a tangent). In this way, both the position and also both spatial angles of the entry point (e.g., the puncture location) are known from the course of the vessel. The two spatial angles may include the azimuthal angle and the altitude angle. Registering the item of patient information with the medical device (e.g., the C-frame X-ray device) provides the information on placement of the entry point in the coordinate system of the medical device. In the case of a rigid geometry of the motion device (e.g., a catheter robot and/or a vascular navigation robot), the position and alignment thereof may be fully determined using an alignment of a front unit of the motion device. The position and alignment of the front unit may be determined using the placement of the entry point (e.g., the position and the two spatial angles). Using the item of information on the geometry of the motion device that is contained in the item of object information OI, it is possible to determine the placement of the motion device (e.g., the position and external envelope of the motion device). Since the position and envelope of the motion device in the coordinate system of the C-frame X-ray device are known as a result of registration, for the purpose of avoiding collision, the position and envelope of the motion device may be incorporated into the collision model CM, favorably with an appropriate error tolerance.

Figure 3:
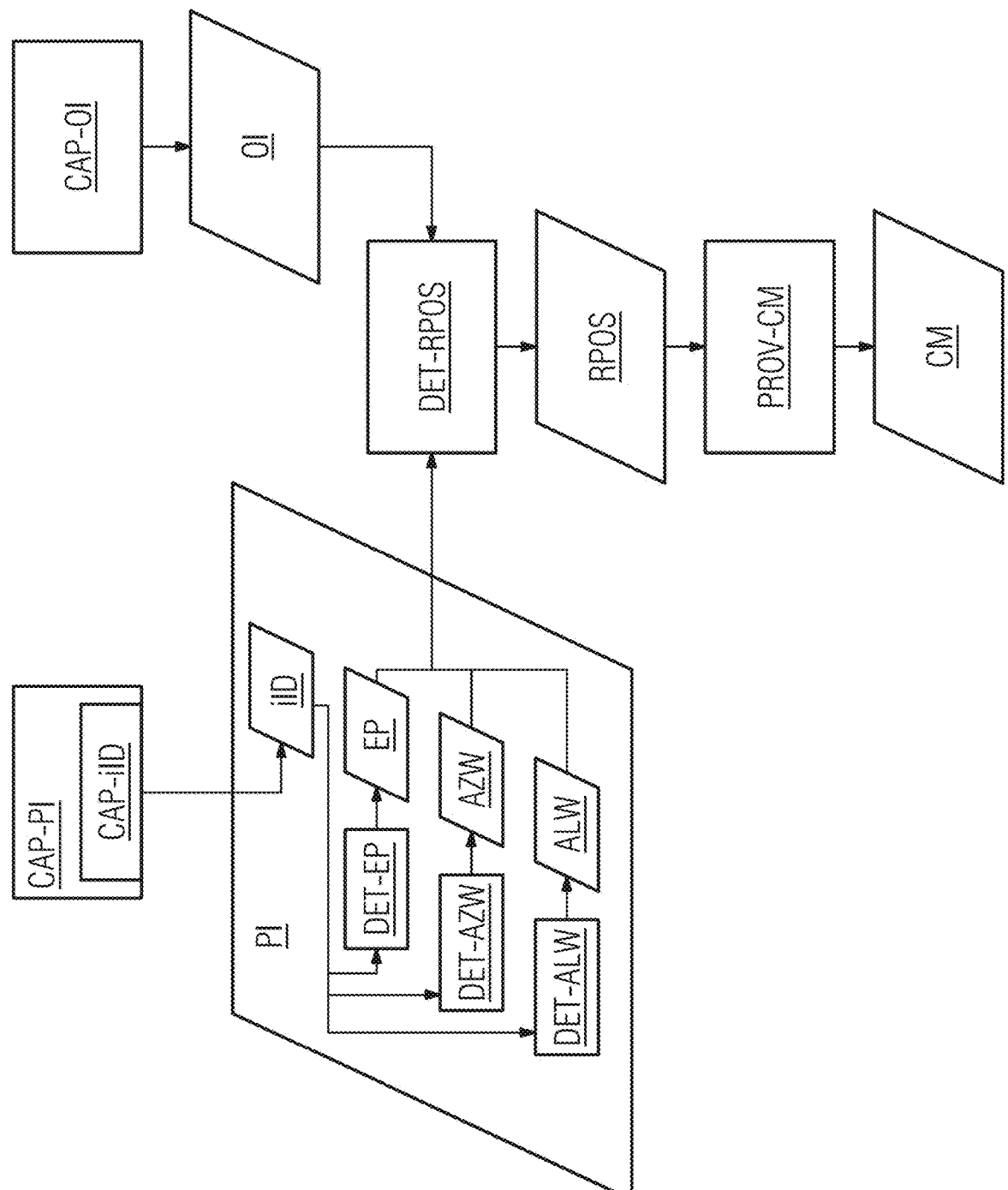

FIG. 3 schematically illustrates a further embodiment of the method for providing a collision model PROV-CM. In this context, detection of the item of patient information CAP-PI may include capture and/or receiving CAP-iID of intraoperative image data iID of the object undergoing examination. Further, it is possible to identify, in the intraoperative image data iID, imaging of at least one portion of the medical object and/or imaging of the introducer sheath for introducing the medical object into the object undergoing examination. In this context, the position of the entry point EP may be determined DET-EP using the identified imaging.

Identification of the imaging of the at least one portion of the medical object and/or the introducer sheath in the intraoperative image data iID may include identification of a marker structure. In this context, the item of object information may have an item of information on a geometry and/or arrangement of the marker structure on the medical object and/or the introducer sheath.

If a two-dimensional (2D) imaging of the introducer sheath is identified in the intraoperative image data iID, then using the imaging, a spatial position P and an azimuthal angle AZW of the introducer sheath may be determined DET-P and DET-AZW. In this context, the item of object information OI may have an item of information on a geometry of the introducer sheath. Further, using the 2D imaging of the introducer sheath and the item of object information, it is possible to determine an altitude angle ALW of the introducer sheath DET-ALW. The relative placement RPOS may be determined DET-RPOS based on the position P of the introducer sheath, the azimuthal angle AZW, the altitude angle ALW, and the item of object information OI.

As an alternative, the intraoperative image data iID may have at least two images of the at least one portion of the medical object and/or at least two images of the introducer sheath, respectively from different imaging directions. In this context, a spatial position and alignment of the at least one portion of the medical object and/or the introducer sheath may be determined using the respective at least two images. Further, the relative placement RPOS may be determined DET-RPOS based on the position and alignment of the at least one portion of the medical object and/or the introducer sheath and the item of object information OI.

Described below is an example of a sequence of the above-described embodiment of the proposed method, with the intraoperative image data iID including a single X-ray projection image (e.g., anterior-posterior (AP)). In a first act, the azimuthal angle AZW of the introducer sheath (e.g., a vascular introducer sheath) may be determined DET-AZW. The introducer sheath is readily visible in the X-ray projection image. In the case of an AP-captured X-ray projection image, by identifying the introducer sheath, it is possible to make a direct deduction of the 2D position P(AP) and the azimuthal angle AZW. The height of a tip of the introducer sheath above a patient support device may be assumed to be approximately constant, with the result that, overall, a 3D position P(X,Y,Z) of the tip of the introducer sheath is known. In a second act, the altitude angle ALW of the introducer sheath may be determined DET-ALW. By comparing a length Lp of the image of the introducer sheath in the X-ray projection image with an original length Lo of the introducer sheath, which is known from the item of object information, it is possible to deduce the altitude angle ALW:

$$\cos(ALW) = \frac{Lo}{Lp}.$$

If a conical ray projection is used to generate the X-ray projection image, small deviations may occur.

If a marker structure (e.g., an X-ray-opaque structure such as a wire frame) is arranged on the introducer sheath, then determination of the position P, the azimuthal angle AZW, and the altitude angle ALW may be simplified. In one embodiment, the item of object information may have an item of information on the geometry of the marker structure. For example, the marker structure may have a wire cage with at least one (e.g., a plurality) of radiopaque balls. In this context, a marker ball may be arranged at the top, on the introducer sheath. A plurality of grading balls may be arranged below the introducer sheath, an angle being associated with each grading ball. The azimuthal angle AZW may be estimated depending on the projection of the marker ball on the grading ball. By extending the grading balls in the lateral direction, it is also possible to estimate the altitude angle ALW.

The position and alignment of the front unit may be determined (e.g., unambiguously) using the position P of the tip of the introducer sheath and the two spatial angles AZW and ALW. Using the item of information on the geometry of the motion device that is contained in the item of object information OI, it is possible to determine the placement of the motion device (e.g., the position and external envelope of the motion device). Since the position and envelope of the motion device in the coordinate system of the C-frame X-ray device are known as a result of registration, for the purpose of avoiding collision, the position and envelope of the motion device may be incorporated into the collision model CM, favorably with an appropriate error tolerance.

Figure 4:
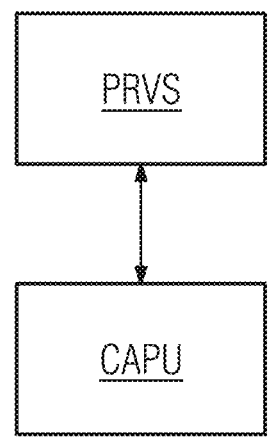
FIGS. 4 and 5 show schematic illustrations of different embodiments of a system.

FIG. 4 shows a diagrammatic illustration of an embodiment of a system of the present embodiments. In this context, the system may include a detection unit CAPU and a providing unit PRVS (e.g., formed by one or more processors). The system may be configured to perform a method of the present embodiments for providing a collision model PROV-CM. Further, the detection unit CAPU may be configured to detect the item of patient information CAP-PI and the item of object information CAP-OI. The providing unit PRVS may be configured to determine the relative placement DET-RPOS and to provide the collision model PROV-CM.

Figure 5:
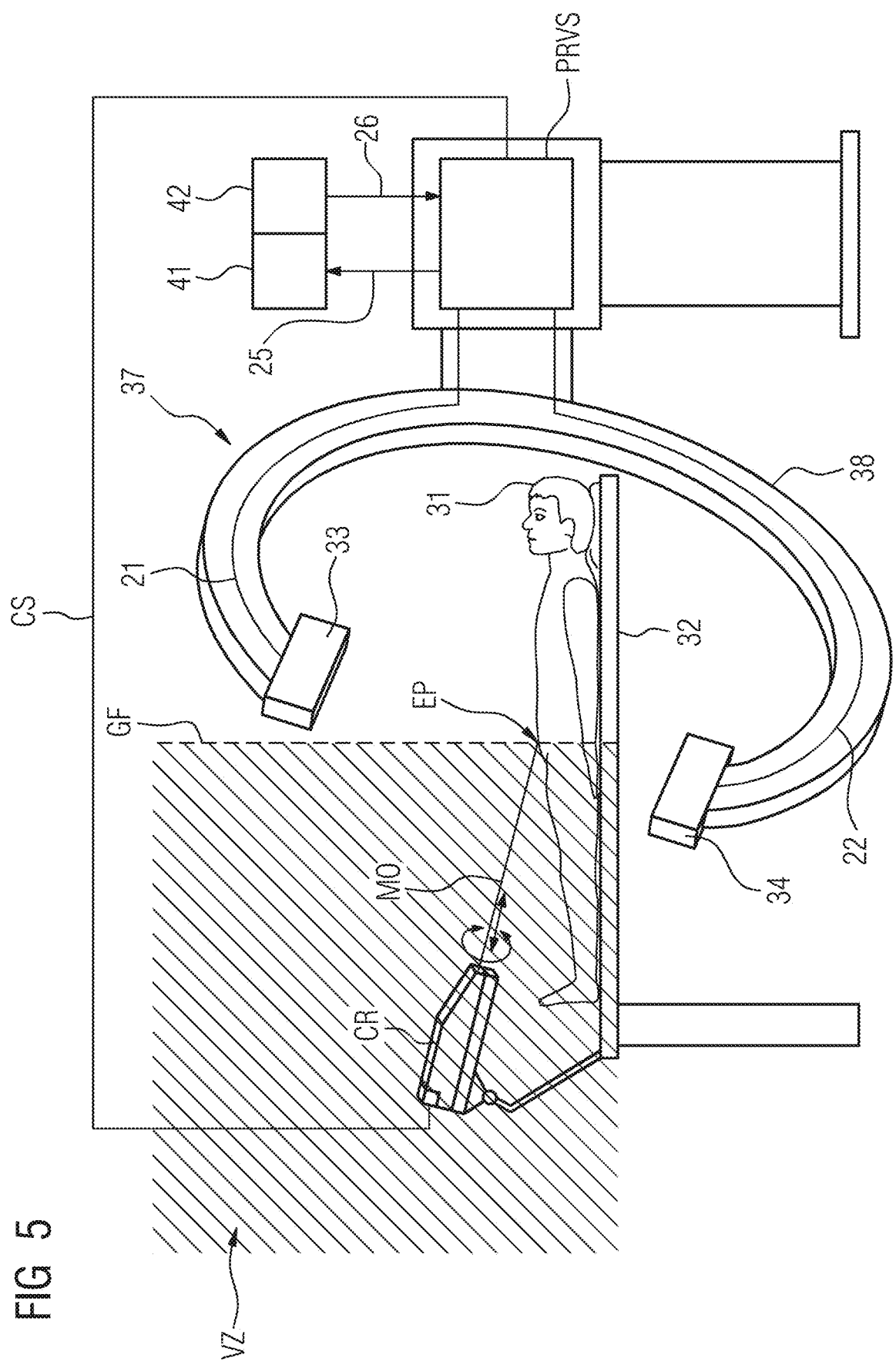

FIG. 5 schematically illustrates a further embodiment of the system of the present embodiments. In this context, the system may also include the medical device, which is configured to be moved depending on the collision model CM, such that no contact is made between the medical device, the manipulator, and the medical object MO. In FIG. 5, the medical device includes a medical imaging device. In this context, the medical imaging device may include, for example, a medical C-frame X-ray device 37.

The medical C-frame X-ray device 37 may have a detector 34 (e.g., an X-ray detector) and a source 33 (e.g., an X-ray source) that are arranged in a defined arrangement on a C-arm 38. The C-arm 38 of the C-frame X-ray device 37 may be mounted to be movable about one or more axes. For the purpose of capturing the preoperative and/or intraoperative image data of the object undergoing examination 31, which is placed on a patient support device 32, the providing unit PRVS may send a signal 24 to the X-ray source 33. Then, the X-ray source 33 may emit an X-ray beam. When, after interacting with the object undergoing examination 31, the X-ray beam impinges on a surface of the detector 34, the detector 34 may send a signal 21 to the providing unit PRVS. The providing unit PRVS is able to detect the preoperative and/or intraoperative image data via the signal 21.

In one embodiment, the manipulator may include a motion device CR for remote manipulation of the medical object MO by robot. In an operating condition of the system, the distal portion of the medical object MO may be at least partly arranged in the object undergoing examination 31. For example, in the operating condition of the system, the distal portion of the medical object MO may be introduced into the object undergoing examination 31 at the entry point EP via the introducer sheath. Further, the motion device CR may be secured (e.g., movably) to the patient support device 32 by a securing unit such as a stand and/or robot arm. In this context, the motion device CR may have a defined positional relationship relative to the patient support device 32. Further, the relative placement RPOS may also be determined DET-RPOS based on the defined positional relationship. In one embodiment, the motion device CR may be configured to move the medical object MO in translation at least along a direction of longitudinal extent of the medical object MO. In the operating condition of the system, the medical object MO is at least partly arranged in the motion device CR. Further, the motion device CR may be configured to rotate the medical object MO about the direction of longitudinal extent of the medical object MO.

In one embodiment, providing the collision model PROV-CM may include identification of a forbidden spatial zone VZ in which the motion device CR is at least partly (e.g., fully) arranged. In this context, movement of the C-frame X-ray device 37 (e.g., a movement of the C-arm 38) may be controlled using the collision model CM such that the C-frame X-ray device does not penetrate into the forbidden zone VZ and/or become arranged in the forbidden zone VZ. In one embodiment, the collision model CM may additionally be provided PROV-CM based on the item of object information M. In this context, the forbidden zone VZ may be identified using the geometry of the motion device CR. For example, the forbidden zone VZ may be delimited by a boundary face GF that runs through the entry point EP (e.g., through the tip of the introducer sheath). For example, the forbidden zone VZ may include an infinite half-space that is delimited by the boundary face GF.

Further, the system may have an input unit 42 such as a keyboard, and a representation unit 41 such as a monitor and/or a display and/or a projector. The input unit 42 may be integrated into the representation unit 41 (e.g., in the case of a capacitive and/or resistive input display). The input unit 42 may be configured to detect a user input. To do this, the input unit 42 may send, for example, a signal 26 to the providing unit PRVS. The providing unit PRVS may be configured to be controlled depending on the user input (e.g., the signal 26, such as for performing a method for providing a collision model PROV-CM. As an alternative or in addition, the providing unit PRVS may be configured to control movement of the C-frame X-ray device 37 using the user input. Further, the providing unit PRVS may be configured to control the motion device CR (e.g., the robotic movement of the medical object MO) by a signal CS (e.g., depending on the user input). In one embodiment, the representation unit 41 may be configured to display a graphic representation of the collision model and/or a warning signal and/or a workflow indicator and/or the preoperative image data and/or the patient model and/or the intraoperative image data. To do this, the providing unit PRVS may send a signal 25 to the representation unit 41.

The schematic illustrations in the described figures are not in any way to scale or indicative of relative size.

In the context of the present application, the expression "on the basis of" may be understood, for example, in the sense of the expression "with the use of". For example, wording according to which a first feature is generated (or alternatively, determined, etc.) based on a second feature does not rule out the possibility that the first feature may be generated (or alternatively, determined, etc.) based on a third feature.

The methods that are described in detail above and the illustrated devices are merely embodiments that may be modified by those skilled in the art in the greatest variety of ways without departing from the scope of the invention. Further, use of the indefinite article "a" or "an" does not rule out the possibility that a plurality of the features concerned may also be present. Similarly, the terms "unit" and "element" do not rule out the possibility that the components concerned include a plurality of cooperating component parts that may, where appropriate, also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for providing a collision model, the method comprising:
   detecting an item of patient information that has information on a spatial placement of an entry point of a medical object into an object undergoing examination and information on alignment of the entry point of the medical object into the object undergoing examination, wherein the item of patient information is registered with a medical device that is movable;
   detecting an item of object information that has an item of information on a geometry and spatial position of a manipulator for moving the medical object, wherein the manipulator comprises a motion device, a member of technical medical personnel, or the motion device and the member of technical medical personnel;
   determining a relative placement of the manipulator in relation to the object undergoing examination based on the item of patient information and the item of object information; and
   providing the collision model for the purpose of moving the medical device based on the relative placement and the item of object information.

2. The method of claim 1, wherein detecting the item of patient information comprises capturing, receiving, or capturing and receiving preoperative image data, a patient model, or the preoperative image data and the patient model of the object undergoing examination,
   wherein an item of planning information on a planned procedure, a planned placement of the entry point, or a combination thereof is detected, and
   wherein the position of the entry point is determined using the item of planning information and the preoperative image data, the patient model, or the preoperative image data and the patient model.

3. The method of claim 1, wherein detecting the item of patient information comprises capturing, receiving, or capturing and receiving intraoperative image data of the object undergoing examination,
   wherein imaging of at least a portion of the medical object, imaging of an introducer sheath for introducing the medical object into the object undergoing examination, or a combination thereof is identified in the intraoperative image data, and
   wherein the position of the entry point is determined using the identified imaging.

4. The method of claim 3, wherein a two-dimensional (2D) imaging of the introducer sheath is identified in the intraoperative image data,
   wherein a spatial position and an azimuthal angle of the introducer sheath are determined using the 2D imaging of the introducer sheath,
   wherein the item of object information has information on a geometry of the introducer sheath,
   wherein an altitude angle of the introducer sheath is determined using the 2D imaging of the introducer sheath and the item of object information, and
   wherein the relative placement is determined based on the position of the introducer sheath, the azimuthal angle, the altitude angle, and the item of object information.

5. The method of claim 3, wherein the identification of the imaging of the at least one portion of the medical object, the introducer sheath, or the combination thereof in the intraoperative image data comprises identification of a marker structure, and
   wherein the item of object information has information on a geometry, an arrangement, or the geometry and the arrangement of the marker structure on the medical object, the introducer sheath, or the medical object and the introducer sheath.

6. The method of claim 3, wherein the intraoperative image data has at least two images of the at least one portion of the medical object, at least two images of the introducer sheath, or the at least two images of the at least one portion of the medical object and the at least two images of the introducer sheath, respectively from different imaging directions,
   wherein a spatial position and alignment of the at least one portion of the medical object, the introducer sheath, or the at least one portion of the medical object and the introducer sheath are determined using the respective images, and wherein the relative placement is determined based on the position and alignment of the at least one portion of the medical object, the introducer sheath, or the at least one portion of the medical object and the introducer sheath, and the item of object information.

7. The method of claim 1, wherein the item of object information comprises information on a geometry of an external shape of the manipulator, a placement of the medical object on the manipulator, or a combination thereof.

8. The method of claim 1, wherein the object undergoing examination is arranged on a patient support device, wherein the manipulator has a defined positional relationship relative to the patient support device, and wherein the relative placement is also determined based on the defined positional relationship.

9. The method of claim 1, wherein the medical device comprises a medical imaging device, a medical treatment device, or a medical imaging and medical treatment device.

10. The method of claim 1, wherein a movement of the medical device is controlled using the collision model, such that no contact is made between the medical device, the manipulator, and the medical object.

11. The method of claim 10, wherein providing the collision model comprises identifying a forbidden spatial zone in which the manipulator is at least partly arranged, and wherein a movement of the medical device is controlled using the collision model, such that the medical device does not penetrate into the forbidden zone, become arranged in the forbidden zone, or penetrate into the forbidden zone and become arranged in the forbidden zone.

12. The method of claim 11, wherein providing the collision model is also based on the item of object information, and wherein the forbidden zone is identified using the geometry of the manipulator.

13. The method of claim 12, wherein the forbidden zone is identified as conical, cuboid, ellipsoidal, a half-space, or any combination thereof.

14. The method of claim 1, wherein the entry point of the medical object into the object undergoing examination includes an entry site of the medical object into the object undergoing examination and an entry channel of the medical object into the object undergoing examination, and wherein the information on the spatial placement of the entry point includes information on a spatial position of the entry site, and the information on the alignment of the entry point includes information on spatial alignment of the entry channel.

15. A system comprising:

one or more sensors configured to:

detect an item of patient information that has information on a spatial placement of an entry point of a medical object into an object undergoing examination and information on alignment of the entry point of the medical object into the object undergoing examination, wherein the item of patient information is registered with a medical device that is movable; and detect an item of object information that has an item of information on a geometry and spatial position of a manipulator for moving the medical object, wherein the manipulator comprises a motion device, a member of technical medical personnel, or the motion device and the member of technical medical personnel; and a processor configured to:

determine a relative placement of the manipulator in relation to the object undergoing examination based on the item of patient information and the item of object information; and provide the collision model for the purpose of moving the medical device based on the relative placement and the item of object information.

16. The system of claim 15, further comprising the medical device, wherein the medical device is configured to be moved depending on the collision model, such that no contact is made between the medical device, the manipulator, and the medical object.

17. The system of claim 16, wherein the medical device comprises a medical imaging device, a medical treatment device, or a medical imaging and medical treatment device.

18. The system of claim 15, wherein the one or more sensors include an object sensor, a patient sensor, or the object sensor and the patient sensor.

* * * * *